United States Patent

Stuebe et al.

Patent Number: 5,659,538
Date of Patent: Aug. 19, 1997

[54] DIAPER REGISTRATION CONTROL SYSTEM

[75] Inventors: Myron Lee Stuebe; James Michael Fleming, both of Cincinnati; Mark David Whaley, West Chester, all of Ohio

[73] Assignee: The Procter & Gambel Company, Cincinnati, Ohio

[21] Appl. No.: 410,993

[22] Filed: Mar. 27, 1995

[51] Int. Cl.$^6$ .................................. G06F 19/00
[52] U.S. Cl. ........................ 364/469.02; 83/371
[58] Field of Search ........................ 364/469, 471, 364/496.01, 496.03, 469.04, 471.01, 471.02, 274.09; 83/365, 370, 371, 76.7, 76.8; 428/74

[56] References Cited

U.S. PATENT DOCUMENTS

| | | | |
|---|---|---|---|
| Re. 35,067 | 10/1995 | Bauknecht | 493/11 |
| 4,264,957 | 4/1981 | Pautzke | 364/469.04 |
| 4,279,369 | 7/1981 | Passafiume | 225/3 |
| 4,361,269 | 11/1982 | Hanlan | 226/30 |
| 4,415,978 | 11/1983 | Craemer et al. | 364/474.09 |
| 4,426,898 | 1/1984 | Friberg | 83/37 |
| 4,449,433 | 5/1984 | Miyamoto | 83/371 |
| 4,669,344 | 6/1987 | Herrig | 83/27 |
| 4,680,205 | 7/1987 | Lerner et al. | 428/29 |
| 4,719,575 | 1/1988 | Gnuechtel | 364/469.01 |
| 4,719,855 | 1/1988 | Cannon et al. | 101/426 |
| 4,736,446 | 4/1988 | Reynolds et al. | 382/112 |
| 4,737,904 | 4/1988 | Ominato | 364/167.01 |
| 4,757,930 | 7/1988 | Ditto | 226/27 |
| 4,781,090 | 11/1988 | Feldkamper et al. | 83/74 |
| 4,795,510 | 1/1989 | Wittrock et al. | 156/64 |
| 4,837,715 | 6/1989 | Ungpiyakul et al. | 364/552 |
| 4,847,775 | 7/1989 | Roch et al. | 364/469 |
| 4,955,265 | 9/1990 | Nakagawa et al. | 83/74 |
| 4,961,149 | 10/1990 | Schneider et al. | 364/470.06 |
| 4,994,975 | 2/1991 | Minshcart | 364/469.04 |
| 5,016,182 | 5/1991 | Bergland et al. | 364/469.04 |
| 5,045,135 | 9/1991 | Meissner et al. | 156/64 |
| 5,119,725 | 6/1992 | Okamura | 101/226 |
| 5,235,515 | 8/1993 | Ungpiyakul et al. | 364/469.04 |
| 5,249,139 | 9/1993 | Blasius et al. | 364/526 |
| 5,286,543 | 2/1994 | Ungpiyakul et al. | 428/74 |

*Primary Examiner*—Reba L. Elmore
*Assistant Examiner*—Steven R. Garland
*Attorney, Agent, or Firm*—Dinsmore & Shohl LLP

[57] ABSTRACT

The automatic registration control system of the present invention is a closed loop system including a driving mechanism for feeding a continuous web of disposable absorbent articles, such as diaper pads, toward a cutter. The cutter may separate completed pads from the web. A sensor is positioned along the manufacturing line, and preferably preceding the cutter, for detecting at least one preselected feature of each diaper pad and producing a detection signal when the feature passes by the sensor. A position resolver determines the angular position of the cutter at the moment when the preselected diaper feature is detected, and the average angular position is calculated from a predetermined number of cutter positions. The average cutter position is compared to and subtracted from a target cutter position to produce an error signal. The error signal is then converted into a control signal and supplied to a phase variator which adjusts the position of the cutter in response to the control signal.

20 Claims, 3 Drawing Sheets

DIAPER REGISTRATION CONTROL SYSTEM

FIELD OF THE INVENTION

This invention relates generally to a registration control system and more particularly to a closed-loop registration control system and method for controlling the location of a rotary knife cut on a web of material. The invention will be specifically disclosed in connection with a system for varying the angular position of a rotary cutter to change the phase relationship between the cutter and a preselected feature on a continuous web of interconnected diaper pads.

BACKGROUND OF THE INVENTION

In the manufacturing of disposable absorbent articles, such as diapers, adult incontinence articles, and sanitary napkins, it is a common manufacturing practice to initially fabricate a plurality of individual articles, such as diapers, that are serially spaced in interconnected positions on a continuous web. Individual diapers thereafter are formed by directing the web into a rotary cutter to cut the web between the spaced pads, usually as the final cutting operation in the manufacturing process.

In order to produce uniform diapers, and to eliminate waste, it is desirable to control relatively precisely the location at which the web is severed (typically referred to as the "final cut"). It is particularly desirable to cut the web in a correct position relative to features that are formed on the diaper. For example, disposable diapers frequently use adhesive tab strips and it is desirable to control the distance between these tabs and the top of the diaper within a relatively narrow tolerance.

Controlling the location of the final cut relative to other diaper features in an economically viable way has been and continues to be problematic for diaper manufacturers. Variation in the placement of the knife cut is inherent in the diaper manufacturing line equipment due to a number of factors including equipment wear, variations in raw materials, etc. Such variation in the final cut results in sequential pads that alternate between long and short lengths. Web tension and temperature variations also occur when the pull rolls in the manufacturing line expand or contract as the line is placed into production. The increase in temperature makes the roll softer, allowing the web to compress the rolls. As the rolls are compressed, the surface of the roll increases, increasing the circumference of the roll. This results in an increase in the web speed through the roll. The diaper pads are advanced into the final knife with the increased effective pull roll speed, and as a result, beginning from a cold start, the final cut distance can shift significantly.

The variation in the final knife placement may steadily trend from one side of the specification limit to the other in a smooth transition, therefore making the detection of unacceptable variation difficult. Detecting unacceptable variation was previously left to the operators of the production line. This has been proven to be unacceptable in many instances because the variation can go undetected. Even when the variation can be detected by the line operator, it is usually at a point in time where an unacceptable level of product must be scrapped. Furthermore, inefficiencies are created because once the unacceptable variation is detected, the operator must manually adjust the system to correct the final knife placement.

Automatic registration control systems have been employed in web processing apparatus to overcome the problems of manual detection. For example, automatic registration control systems have been used in the manufacturing of price tags. In these systems, the tag web being fed is cut while its cut position is constantly corrected by a rotary blade. The blade is adjusted so that it can cut a variety of price tag webs having different cutting pitches or intervals. In these systems, after a tag is detected having a new cutting distance, the cutter is adjusted to correspond to the correct cutting position. This type of system has not been used in controlling the knife placement along the diaper web because the systems were not designed to accommodate extensible webs used in diaper production, but rather were designed as a means for adjusting the knife when a new cutting pitch or interval was necessary.

Attempts also have been made to control the rate at which a diaper web is fed to the cutter. However, this type of registration control system is undesirable because it requires multiple sensors located along the web, increasing the complexity of the registration system. In addition, adjusting the web speed produces additional tensile stresses on the web by constantly changing the speed at which it is fed to the cutter. Considering that web tension problems are already inherent in diaper manufacturing lines, this problem is compounded by control systems which maintain the registration by continually adjusting the web speed.

Therefore, there exists a need for an automatic registration control system that controls the placement of the final cut with respect to a pre-selected feature of the diaper which eliminates the problems associated with previous registration control methods.

SUMMARY OF THE INVENTION

The present invention provides an automatic registration control system which eliminates the problem of excessive variation in the placement of the final cut that separates an individual disposable absorbent article, such as a diaper, from a continuous web of completed pads. The automatic registration control system of the present invention is a closed loop system that includes a driving mechanism for feeding a continuous web of diaper pads toward a rotary cutter. A sensor is positioned along the manufacturing line upstream or downstream of the rotary cutter for detecting at least one preselected feature of each diaper pad and producing a detection signal when the feature passes by the sensor. A position resolver determines the angular position of the rotary cutter at the moment when the preselected diaper feature is detected, and the average angular position is calculated from a predetermined number of cutter positions. The average cutter position is compared to and subtracted from a target cutter position to produce an error signal. The error signal is then converted into a control signal and supplied to a phase variator which adjusts the rotational position of the rotary cutter in response and proportionally to the control signal.

The target cutter position is present at a value determined by an operator, who must manually advance or retard the phase of the final knife until the final cut is in the proper location. Once the proper registration has been achieved, the operator switches over the line to automatic mode. A new target position is then calculated by using the knife positions corresponding to the first 25 pads to be scanned by the sensor. An average knife position is continually calculated using the 25 most recent positions stored in memory as scanned by the sensor.

Any deviation of the average knife position from the target value results in the error signal being supplied to a proportional compensator, which generates the control signal. The control signal is then supplied to a velocity controlled servo, which in turn drives, through a gear box, a correction shaft of the phase variator. The phase variator either advances or retards the phase of the final knife so as to bring the error closer to zero. The control system detects and adjusts to any changes in the average placement of the final cut.

Consequently, it is an object of the invention to reduce the variation in the placement of a knife cut with respect to a preselected diaper feature by controlling the angular position of a rotary cutter based upon the average angular position of the rotary cutter when the preselected feature is detected.

BRIEF DESCRIPTION OF THE DRAWINGS

Other objects and advantages of the invention will become apparent upon reading the following detailed description and upon reference to the drawings, in which it is understood to be illustrated by a diaper control system, but generally applicable to disposable absorbent article control systems.

DETAILED DESCRIPTION OF THE PREFERRED EMBODIMENT

The present invention has been designed to reduce the variation in the placement of a knife cut along the continuous diaper web using the approach of a closed loop registration control system. The system may also be used to control the relative positions of any two features of the diaper, so that one feature may be operated on, e.g. by attachment to the diaper, cutting from stock, calendaring, straining, printing, spinning, etc., in special relationship relative to the other feature.

Figure 1:
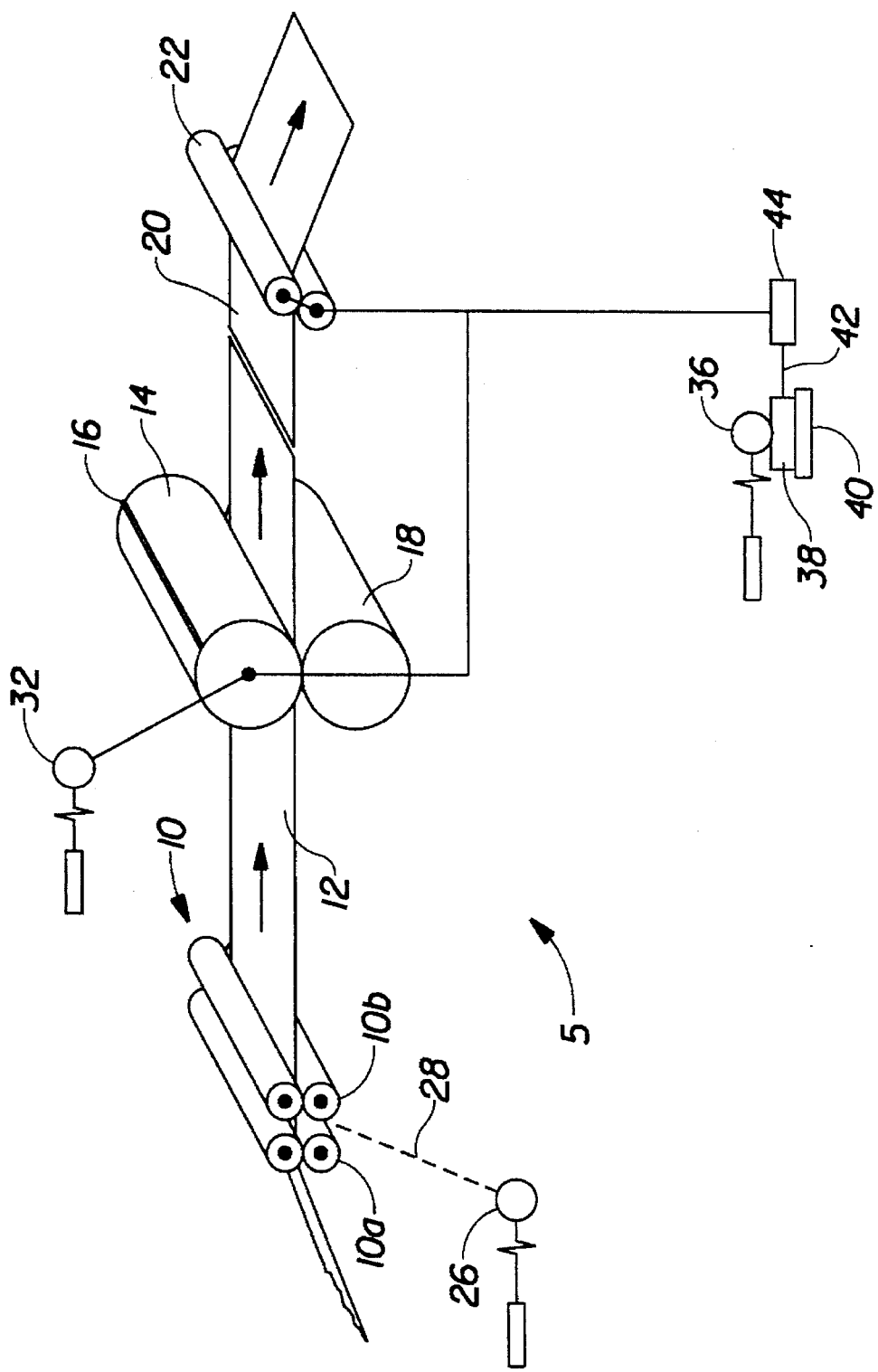
FIG. 1 is a schematic diagram of the final knife cutting operation of a diaper line.

FIG. 1 illustrates the invention as incorporated in controlling the placement of the knife cut in relation to the diaper fastening tabs. In FIG. 1, the control system 5 includes two sets of pull rolls 10 for feeding a continuous web 12 of diaper pads along a path towards knife 14. Pull rolls 10 are mechanically driven at a preselected speed by external means (not shown). The knife includes a blade 16 positioned along the surface of the knife which rotates above an anvil 18 for separating a completed diaper 20 from the web 12. The separated diaper 20 continues through nip rolls 22 to a final folding station (not shown).

Figure 2:
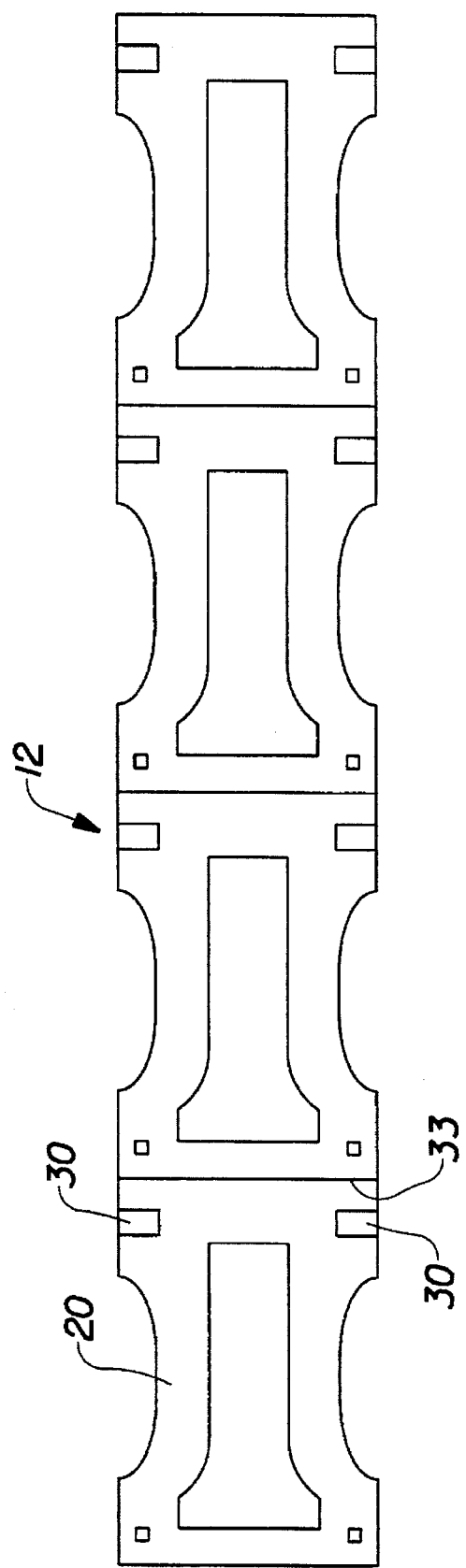
FIG. 2 is a top view of a diaper web wherein the diapers include a fastening system and a core.

The registration control system 5 further includes an ultraviolet luminescence scanner 26, preferably positioned between or after pull roll sets 10a and 10b, and selected to detect at least one preselected feature of each diaper 20 on the web 12 as it passes beneath the scanner 26. The preferred scanner 26 is an optical sensor, such as an Optics LUT 1-4 sensor, manufactured by Sick Co., that emits a modulated ultraviolet light beam 28 towards the web. The ultraviolet luminescence scanner 26 works well for a luminescing preselected feature, against a nonluminescing background. When the preselected feature, such as when fastening tabs 30 pass beneath the ultraviolet beam 28, the tabs emit light at the same modulated frequency as the scanner 26. If the preselected feature and the background have different opacities, an infra-red scanner may be selected. The diaper feature selected for detection may be the fastening tabs 30, as shown in FIG. 2, or may be the edge of the core, or the dedicated fastening surface, etc. The scanner 26 produces a detection signal when it detects a change in the light emitted by, reflected by, absorbed by, or transmitted through the preselected feature.

The scanner 26 should be mounted as near the knife 14 as practical because, as the unit is placed closer to the final cut 33, the control system 5 will better detect changes occurring upstream, and hence become more accurate at predicting the point of cut in relation to the fastening tabs 30. The exact position of the scanner 26 must be balanced with the convenience of mounting the scanner along the line and its likelihood of contamination in various locations.

The angular position of the rotary knife 14 is determined by means of a position resolver 32 which reads the angular position of the knife at the time the fastening tabs are detected by the scanner 26. The angular position of the knife 14 is initially set at a target value determined by an operator, who must initially manually advance or retard the phase of the knife until the location of final cut 33 (FIG. 2) is in the proper location with respect to the fastening tabs 30. Once the proper registration has been achieved, the operator switches over the line to automatic mode through a control panel (not shown). Once in automatic mode, at least five diaper pads, and particularly the first twenty-five diaper pads are scanned and the angular position of the cutter is stored and averaged. The average angular position of the cutter represents the average distance between the fastening tabs and the final cut. This average angular position is stored as a new target value which is more accurate than the first manually set target value.

As the web is processed, an average knife position is continually calculated using the twenty-five most recent angular positions of knife 14 and stored in memory as a twenty-five point moving average. Any deviation of the twenty-five point moving average from the new target value results in the generation of an error signal. The error signal is fed into a proportional compensator 36 which generates a control signal. The control signal may be supplied to a fixed velocity servo 38, or more preferably to a velocity controlled servo 38 which drives through a gear box 40 a correction shaft 42 of a phase variator 44, preferably manufactured by Specon Co. The phase variator 44 either advances or retards the rotational phase of the final knife 14 to compensate for the error.

Figure 3:
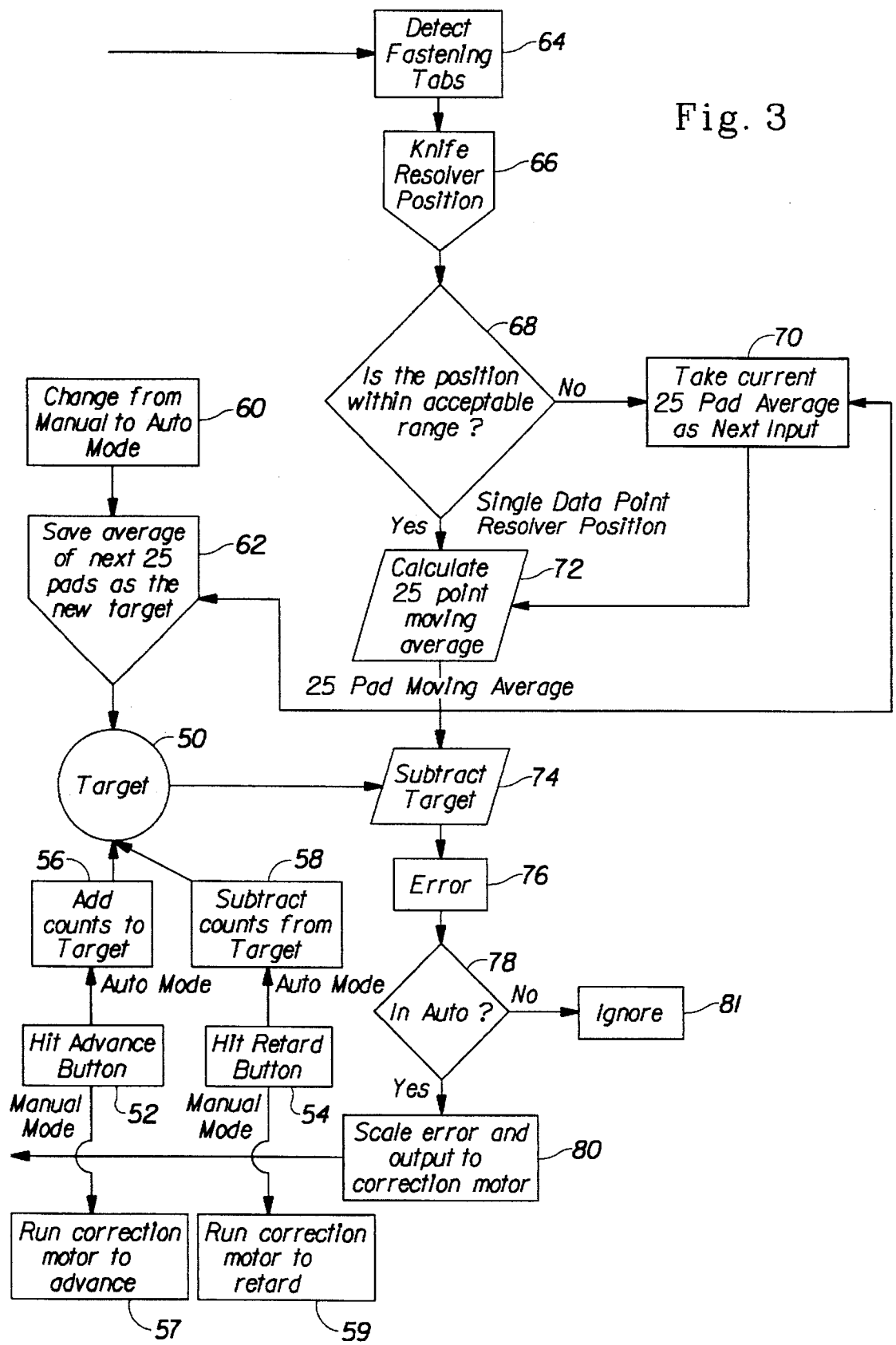
FIG. 3 is a flow diagram of the registration control system of FIG. 1.

Referring now to FIG. 3, the method of controlling the variation in the placement of a knife cut along the continuous web of diaper pads is illustrated. The system has been programmed to perform the following steps. The first step is establishing a target knife position illustrated as block 50. The target knife position 50 is arrived at by manually advancing, illustrated as block 52, or retarding, illustrated as block 54, the phase of the knife, by advancing, illustrated as block 57, or retarding illustrated as block 59, the phase variator which adjusts final knife position. Once the target knife position 50 has been established, the control system is placed in the automatic mode, illustrated as block 60, wherein a new target value, illustrated as block 62, is determined. New target value 62 is the average angular position of the knife calculated from the first twenty-five diaper pads scanned. The target knife position may be adjusted in the automatic mode, as illustrated by block 50 by adding or subtracting counts to or from the target position 50 as illustrated by blocks 56 and 58 respectively.

The next step is detecting, illustrated as block 64, the preselected feature of an individual diaper pad along the continuous web of pads and producing a detection signal as the preselected feature passed beneath the scanner. The angular position of the knife is read, illustrated by block 66, by the position resolver as the fastening tabs are detected. The knife position at the time tabs are detected is compared, illustrated as block 68, to see whether it is within an acceptable range of the new target value. If a knife position datum point is not within the acceptable range, the current twenty-five diaper average, illustrated as block 70, is used as the next data point and the twenty-five point moving average is recalculated using the twenty-five pad average as the new data point and dropping the 26th (oldest) pad datum point as illustrated as block 72. This is done to prevent any one erroneous diaper reading from unduly affecting the twenty-five diaper average and causing an improper change in the position of the knife. The twenty-five point moving average 72 is subtracted, illustrated as block 74, from the new target value 50 to produce an error signal, illustrated as block 76. The error signal is converted, illustrated as block 80, by the proportional compensator into a control signal and supplied to the servo for correction, illustrated as block 80, of the knife position. When the system is not in automatic mode the error is ignored 81.

By computing a twenty-five point moving average, the phase of the knife will be properly adjusted based upon long term variations in the process, rather than any one diaper being improperly cut. Consequently, knife adjustments will be more accurate because they will need to be adjusted less frequently. A predetermined number of diaper pads, e.g. at least 25, may be ignored after start-up of the system. Thus, this number of pads is not used in computing the predetermined average. This allows the system to achieve steady state, thereby minimizing premature adjustments in cutter position.

While the invention has been described in conjunction with the automatic registration control of the knife position with respect to the fastening tabs, dedicated fastening surface or edge of the core, it is to be understood that alternatives, modifications and variations will be apparent to those skilled in the art in light of the foregoing description. For example, the invention can be utilized in other areas of the diaper manufacturing process to control registration of any feature of the diaper relative to another feature of the diaper. Accordingly, the invention is intended to embrace all such alternatives, modifications, and variations as fall within the spirit and broad scope of the appended claims.

What is claimed is:

1. An improved closed-loop registration control system for an absorbent article manufacturing line, said control system comprising:

means for feeding a continuous web of absorbent articles along a path;

a sensor for detecting at least one preselected feature of each of said absorbent articles and producing a detection signal when said preselected feature passes by said sensor;

a cutter for cutting said absorbent articles, said cutter located after said sensor and disposed in a cutter position relative to said preselected feature;

means for determining the cutter position at the moment when said preselected feature is detected;

means for calculating the average of a predetermined number of said cutter positions corresponding to a number of consecutive said absorbent articles which have passed by said sensor for detecting said at least one preselected feature;

means for subtracting a predetermined target cutter position from said average cutter position so as to produce an error signal; and means for converting said error signal into a control signal and supplying said control signal to phase modifying means for said cutter;

wherein said means for modifying the phase of said cutter modifies said cutter position in response to said control signal.

2. The control system of claim 1 wherein said means for modifying the phase of said cutter modifies said cutter position proportionally to said control signal.

3. The control system of claim 2 wherein said sensor comprises an optical scanner.

4. The control system of claim 1 wherein said means for feeding comprises at least one set of pull rolls.

5. The control system of claim 4 wherein said means for feeding comprises two sets of pull rolls and said sensor is positioned between said pull rolls.

6. The control system of claim 1 wherein said means for determining said cutter position comprises a position resolver.

7. The control system of claim 1 wherein said means for modifying the phase comprises a velocity controlled servo and a phase variator.

8. The registration control system of claim 1 wherein said means for feeding a continuous web of absorbent articles moves at a predetermined speed, said cutter position being maintained relative to said preselected feature independently of said predetermined speed.

9. The control system of claim 1, wherein said preselected feature is a functional feature of said absorbent articles.

10. The control system of claim 9 wherein said preselected functional feature of said absorbent article comprises a fastening tab.

11. The control system of claim 9 wherein said preselected functional feature of said absorbent article comprises the edge of the core of said absobent article.

12. An improved method for controlling an angular position of a knife in manufacturing an absorbent article pad from a moving continuous web of absorbent article pads, said method comprising the steps of:

establishing a target knife position for cutting said absorbent article pad;

detecting at least one preselected feature of said absorbent article pad and producing a detection signal as said preselected feature is detected by a detection means;

determining said angular position of said knife when said preselected feature is detected;

storing said angular position of said knife;

comparing said angular position of said knife to said target knife position;

calculating an average knife position from a predetermined number of stored angular positions of said knife to a corresponding number of consecutive absorbent article pads which have been detected by said detection means;

subtracting said target knife position from said average knife position to produce an error signal;

converting said error signal into a control signal and supplying said control signal to a knife position modifying means; and modifying said angular position of said knife in response to said control signal.

13. The method of claim 12 further comprising the step of moving said continuous web of absorbent article pads with respect to said detection means.

14. The method of claim 12 wherein said detecting step further comprises the steps of:

emitting a light beam by said detection means upon said web;

detecting a change in said light beam caused by said preselected feature of said absorbent article pad as said preselected feature moves relative to said detection means; and sensing said change in said light beam.

15. The method of claim 12 wherein said step of modifying said angular position of said knife further comprises the step of driving a phase variator connected to said knife.

16. The method of claim 12 wherein said average knife position is calculated from at least five consecutive absorbent article pads.

17. The method of claim 12 further comprising the step of determining whether said angular position of said knife is inside or outside a predetermined range.

18. The method of claim 17 wherein if said angular position of said knife is outside said predetermined range, said average is used as the next angular position of said knife in calculating said average knife position.

19. The method of claim 18 wherein, after start-up no change in said angular position of said knife is made until a predetermined number of said preselected features have been detected.

20. An improved closed-loop registration control system for controlling the placement of a cut with respect to a preselected feature of an individual absorbent article pad along a continuous web of absorbent article pads, said control system comprising:

at least one pull roll for advancing said continuous web along an absorbent article line;

a knife for performing said cut;

a scanner positioned along said absorbent article line at a location juxtaposed with said knife;

said scanner for detecting and producing a detection signal as said preselected feature passes by said scanner;

a position resolver connected to said knife for determining the angular position of said knife when said preselected feature is detected;

means for subtracting a preselected target knife position from an average knife position, thereby producing an error signal;

a proportional compensator for converting said error signal into a control signal; and a servo, which in response to said control signal, drives a phase variator to correct the placement of said cut.

* * * * *

UNITED STATES PATENT AND TRADEMARK OFFICE
CERTIFICATE OF CORRECTION

PATENT NO. : 5,659,538

DATED : August 19, 1997

INVENTOR(S) : MYRON LEE STUEBE et al.

It is certified that error appears in the above-identified patent and that said Letters Patent is hereby corrected as shown below:

Title page of the issued patent, Assignee:, "Gambel" should read — Gamble —.

Signed and Sealed this

Tenth Day of March, 1998

*Attest:*

BRUCE LEHMAN

*Attesting Officer*  *Commissioner of Patents and Trademarks*